United States Patent [19]

Grabenkort et al.

[11] Patent Number: 5,178,267
[45] Date of Patent: Jan. 12, 1993

[54] PACKAGING SYSTEM FOR A STERILIZABLE CALBRATABLE MEDICAL DEVICE

[75] Inventors: Richard W. Grabenkort, Barrington, Ill.; Conrad T. O. Fong, Redmond; Cheryl D. Germany, Kirkland, both of Wash.

[73] Assignee: Abbott Laboratories, Abbott Park, Ill.

[21] Appl. No.: 631,805

[22] Filed: Dec. 20, 1990

[51] Int. Cl.5 .............................................. B65D 81/18
[52] U.S. Cl. ..................................... 206/210; 53/425; 206/439; 206/570
[58] Field of Search ................................ 206/368-370, 206/210, 438, 570, 461, 803, 439; 53/425

[56] References Cited

U.S. PATENT DOCUMENTS

| | | | |
|---|---|---|---|
| 4,479,761 | 10/1984 | Blistad et al. | 206/570 |
| 4,479,762 | 10/1984 | Blistad et al. | 206/570 |
| 4,522,302 | 6/1985 | Paikoff | 206/570 |
| 4,863,016 | 9/1989 | Fong et al. | 206/210 |
| 4,925,448 | 5/1990 | Bazaral | 206/370 |

*Primary Examiner*—Jimmy G. Foster
*Attorney, Agent, or Firm*—Harry G. Thibault; Robert E. Wexler

[57] ABSTRACT

An improved package for a medical device includes an inner wrap that envelopes the medical device, the inner wrap including a gas-permeable surface, and a chamber defined in the inner wrap to store a hydratable sensor of the medical device. Plumbing for the package controls fluid flow into and within the inner wrap, to selectively establish, without breaching a portion of the inner wrap surrounding the sensor, fluid communication between the gas-permeable surface and the sensor, to sterilize the sensor and the inner wrap with a gaseous sterilant, or to hydrate the sensor with hydration fluid obtained from a source of hydration fluid connected to the chamber, or to equilibrate the hydration fluid in the chamber with an external source of gas, to calibrate the sensor within the inner wrap.

25 Claims, 10 Drawing Sheets

PACKAGING SYSTEM FOR A STERILIZABLE CALBRATABLE MEDICAL DEVICE

TECHNICAL FIELD

This invention relates to packages for and methods of packaging sterilizable, calibratable medical devices, and more particularly, provides an improved packaging system for in situ sterilization and calibration of medical devices comprising hydratable sensor components.

BACKGROUND OF THE INVENTION

U.S Pat. No. 4,863,016, entitled "Packaging for a Sterilizable Calibratable Medical Device", assigned to the assignee of the present invention, describes a package for and method of packaging a sterilizable calibratable medical device that includes a hydratable sensor component. Because the specification of the above noted patent, including the Background of the Invention, is useful to an understanding of the present invention, the specification of U.S. Pat. No. 4,863,016 is hereby incorporated herein by reference.

The medical device referenced in the above noted patent is a blood chemistry sensor that must be maintained in a sterile environment during storage and in a clean environment during the calibration procedure. The packaging provided for the medical device accommodates these requirements. This packaging includes a manifold and a hydration solution pouch, each connected to the sensor component by plumbing. The plumbing also connects the sensor component to the ambient environment of the plumbing. When the packaging is manufactured, the manifold, plumbing, and medical device are sealed in a wrap including a gas-permeable, bacterial retentive surface. The wrap and its contents, including the exterior surfaces of the components, are sterilized by exposure to gaseous ethylene oxide (ETO). During the sterilization procedure, the plumbing is adjusted so that the sensor is exposed to the ambient environment, i.e., the sterilizing gas. After sterilization, the plumbing is adjusted and the medical device is hydrated within the package by directing the hydration solution from the hydration solution pouch to the sensor by means of the plumbing. To allow storage of the package for an extended period of time, a gas-impermeable bag is provided to define a chamber in which the ambient sterile environment of the plumbing is preserved, while the sensor component remains immersed in the hydration solution.

Prior to using the medical device, the sensor component must be calibrated. A portion of the plumbing remote from the sensor component is removed from the packaging. A reservoir including a calibration solution is connected to the plumbing, and the calibration solution is conveyed to the sensor component. As the calibration solution is introduced to the sensor component, the hydration solution is flushed into the manifold via the plumbing. In this manner, the sensor component is calibrated without removing it from the clean environment of the packaging.

The above description reveals one of the problems with the packaging used for the medical device. Before the sensor component can be calibrated, the hydration solution in which it is stored must be removed from the packaging and replaced with the calibration solution. This process introduces several undesirable complications. It would therefore be desirable to calibrate the sensor component without removing it from the clean environment of the package and without removing the hydration solution. The present invention contributes to attaining this objective.

SUMMARY OF THE INVENTION

The present invention provides an improved package for a medical device that includes an inner wrap that envelopes the medical device. The inner wrap includes a gas-permeable, bacterial retentive surface. The device, which includes a hydratable sensor, is stored in a chamber defined within the inner wrap. Fluid flow into and within the inner wrap is controlled by plumbing which is operable to selectively establish, without breaching a portion of the inner wrap surrounding the sensor, fluid communication between the gas-permeable, bacterial retentive surface and the sensor, to sterilize the sensor and the inner wrap with a gaseous sterilant. Fluid communication is also selectively established between the chamber and a source of hydration fluid, to hydrate the sensor or between the chamber and an external source of a gas to equilibrate the hydration fluid, thereby to calibrate the sensor within the inner wrap.

The present invention is better understood by a consideration of a detailed description in conjunction with the drawings provided herewith. A brief description of the drawings is set forth below.

BRIEF DESCRIPTION OF THE DRAWINGS

FIG. 3 is a plan view of the tonometry chamber in the package;

DETAILED DESCRIPTION OF THE PREFERRED EMBODIMENT

Figure 1:
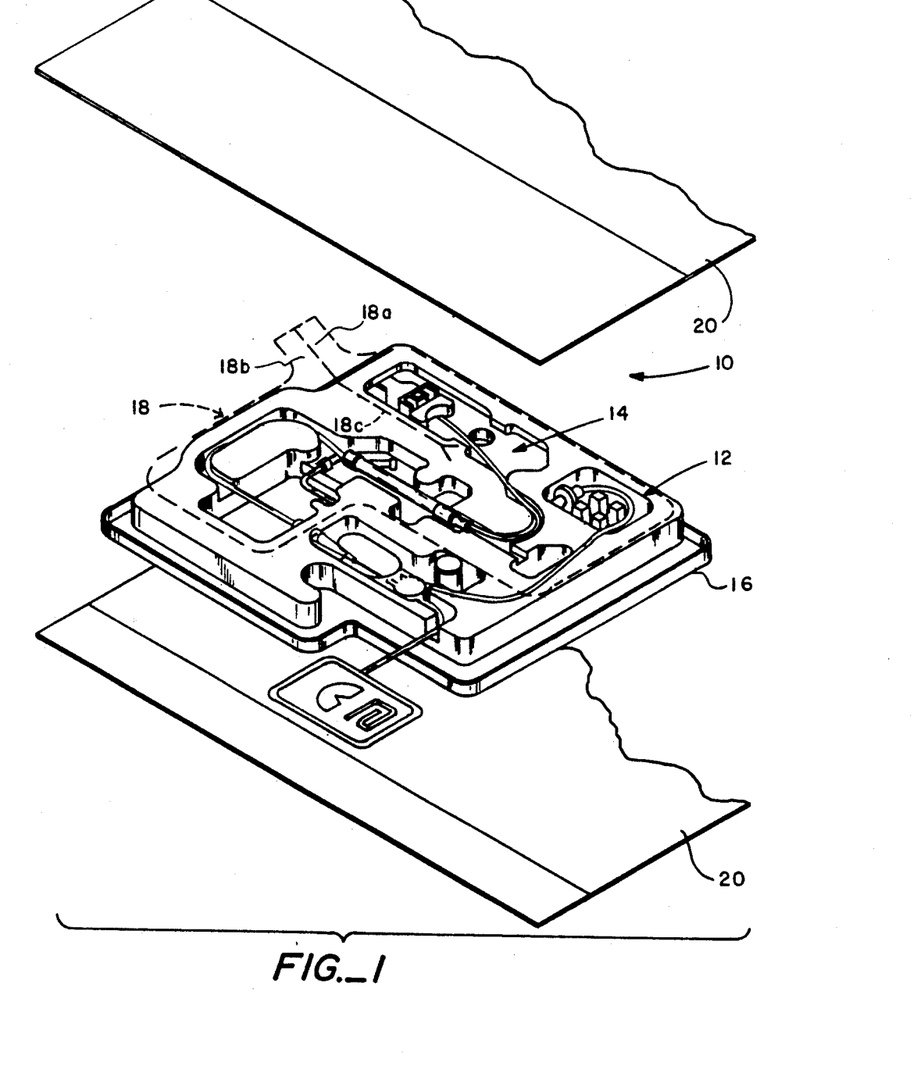
FIG. 1 is an exploded isometric view of a package for a medical device.
Figure 2:
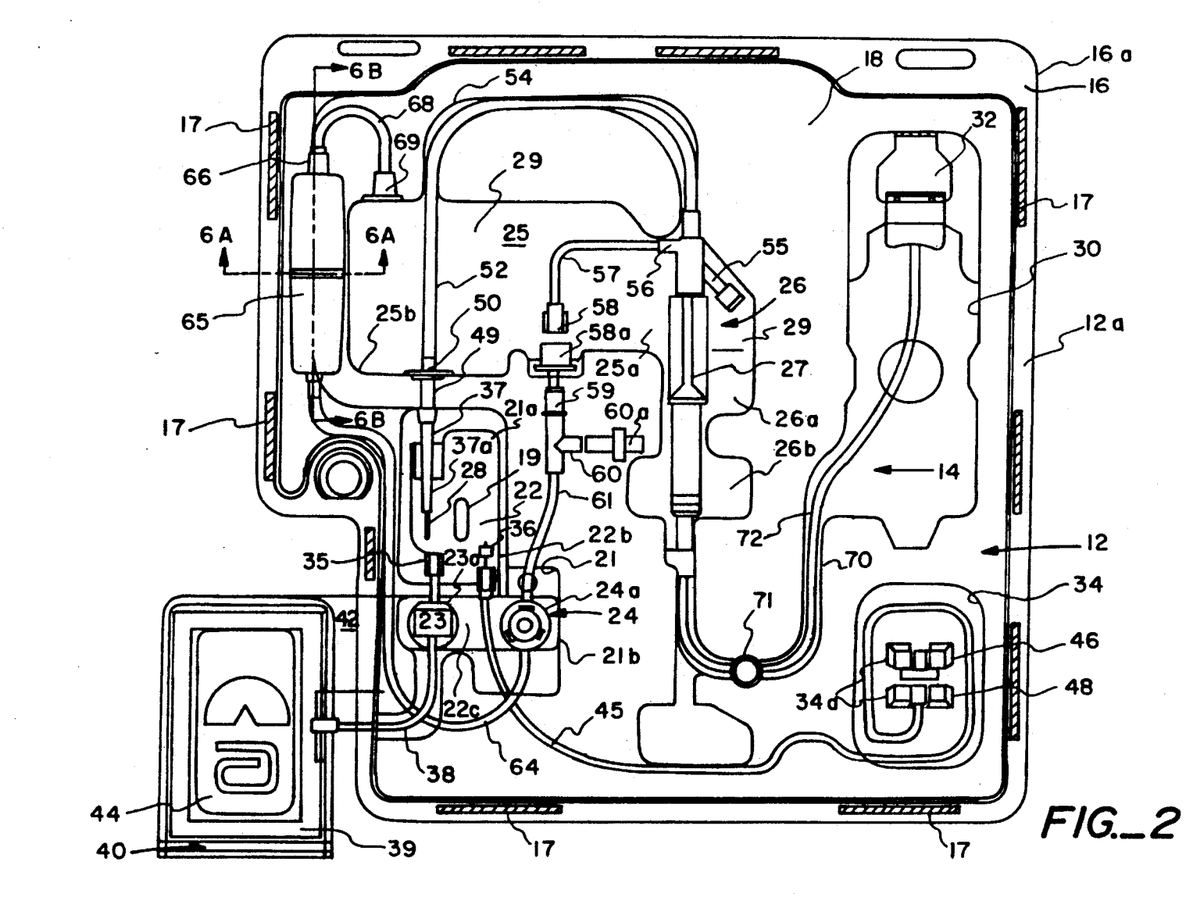
FIG. 2 is a top perspective view of the packaging tray with an attached hydration solution pouch.

With reference to FIG. 1, a preferred embodiment of package 10 includes a packaging tray 12, plumbing 14, a base plate 16 with a peripheral up-turned lip 16a, a gas-permeable, bacterial retentive (Tyvek ™) cover 18, and an outer wrap 20. As shown in FIG. 2, the tray 12 is molded from a clear plastic material and includes a peripheral flange 12a. The tray 12 seats on the base plate 16 and the flange 12a of the tray 12 is secured to the base plate 16 adjacent the lip 16a by a series of ultrasonic welds 17. The tray 12 includes a series of molded-in compartments for holding the various components of the plumbing 14 associated with the package 10. For example, a somewhat L-shaped compartment 21 at the lower left hand corner of the tray 12 as seen in FIG. 2 retains a tonometry chamber 22 in its upright leg 21a. A base leg 21b of the compartment 21 provides space for a guillotine valve 23 and a frangible element valve 24.

Above the compartment 21 is a substantially rectangular compartment 25. To the right of compartments 21 and 25 and connected to compartment 25 at a common inner side wall 25a is an irregularly-shaped, shallow compartment 26, whose base wall 29 engages side wall 25a at a mid-plane thereof, the compartment 26 having separate niches 26a and 26b at a mid-portion thereof, for supporting a delivery device 27 associated with a sensor or sensor component 28 disposed in the tonometry chamber 22. An elongated rectangular compartment 30 is disposed at the right side of the tray 12 for holding a fiber optic connector member 32 associated with the sensor component 28. Located in the lower right hand corner of the tray 12 is a small, rectangular holding compartment 34 for a purpose to be described below.

The tonometry chamber 22 (FIG. 3) is a small, shallow chamber 22 of somewhat ovoid shape, with a flattened outer side walls 22a. A base plate 22b is bonded to a side wall 22a of the chamber 22. The base plate 22b also includes a step portion 22c which extends into the base leg 21b of compartment 21. Receptacles 23a and 24a for retaining the valves 23 and 24 are molded into the step portion 22c.

Figures 3, 3D:
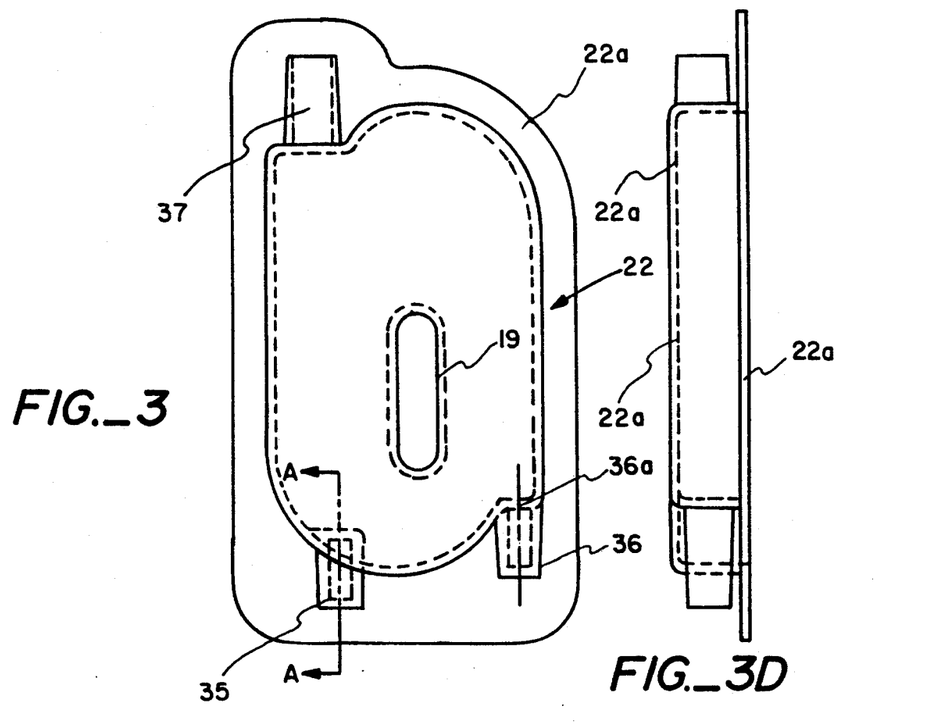
Figure 3A:
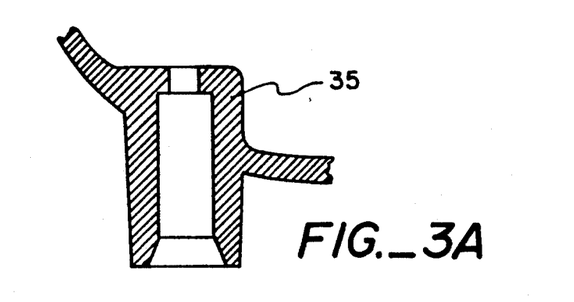
FIG. 3A is a sectional view taken along the lines A—A of FIG. 3, with FIGS. 3B, 3C and 3D being respective top, bottom and side elevations of FIG. 3.
Figure 3B:
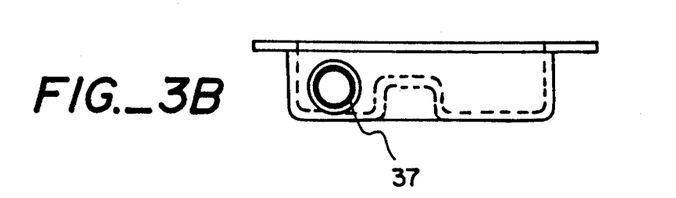
Figure 3C:
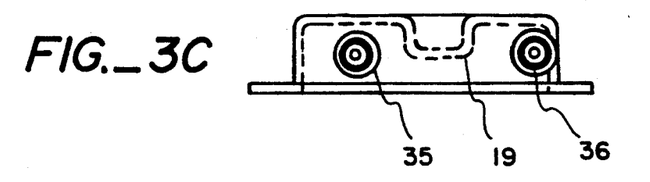

The tonometry chamber 22 also has provided therein a liquid inlet port 35, a gas inlet port 36 and a fluid outlet port 37. The volume of the chamber is relatively small, about 8 ml., to minimize calibration time. A baffle 19 is disposed in the chamber 22, somewhat below the center of the chamber 22, and between the sensor component 28 and the gas inlet port 36. The ovoid shape of the chamber enables a circulatory motion of the hydration fluid in the chamber 22 during calibration. Cannula stock (0.012" OD, 0.005" ID) is mounted in the gas inlet port 36 to provide therein a needle-point orifice 36a to enable calibration gases to bubble into the tonometry chamber 22. A liquid inlet tube 38 connected to the liquid inlet port 35 of the tonometry chamber 22 is connected at its opposite end to a hydration pouch 39 carried within a hydration reservoir 40 disposed externally of the tray 12 and connected thereto by a strap 42 trapped between the tray 12 and the base plate 16. A pouch popper 44 similar to the one disclosed in U.S. Pat. No. 4,683,016 is provided on the reservoir 40. Interposed between the pouch 39 and the liquid inlet port 35 is the guillotine valve 23 described in detail below.

The gas inlet port 36 is connected to tubing 45 which extends to the compartment 34 to be connected to a hydrophobic filter 46 therein. Provided in compartment 34 are molded brackets 34a, which hold the filter 46 in place until it is removed and also to retain when it is re-inserted into the tray 12.

At the upper end of the tonometry chamber 22, the fluid outlet port 37 receives a guide tube 37a for holding the sensor 28 in the chamber 22. The upper end of the fluid outlet port 37 is connected to a flex fitting 49 which extends into the lower end of compartment 25 and is connected to a fastener 50 which connects the fitting 49 to a bottom wall 25b of the compartment 25. The fastener 50 is a fitting which connects the fluid outlet port 37 to a tube 52 which is part of the delivery device 27 and extends through compartment 25 and into a channel 54 which is connected to the upper end of the sensor delivery device compartment 26.

The tubing 52 of the sensor delivery device 27 ends adjacent a Y-fitting 55 of the delivery device 27. A side port 56 of the sensor delivery device 27, opposite and slightly above the Y-fitting 55, extends toward the compartment 25. Tubing 57 connects the side port 56 to fitting 58 which is connected to a bulkhead fitting 58a disposed in the bottom wall 25b of the compartment 25. The fitting 58a in the bottom wall 25b is tilted to facilitate access thereto. Tubing 57 extends into compartment 25 under the side wall 25a. Tubing 59 connects the other side of fitting 58a to one leg of a T-connector 60. Tubing 61 connects the other leg of the T-fitting 60 to one side of the frangible element valve 24. Tubing 64 connects the other side of the valve 24 to an in-line moisture filter or ga filtration device 65.

The in-line moisture filter 65 is supported in the tray 12 adjacent the compartment 25. At its upper end the moisture filter 65 is connected by tubing 68 to a fitting 69 which is mounted in an upper wall 25c of the compartment 25 to vent the output of the in-line moisture filter 65 therein. Gas vented from the filter 65 through the fitting 69 to compartments 25 and 26 passes through the Tyvek ™ cover to the ambient atmosphere outside the tray 12. Connecting channel 70 between the sensor delivery device compartment 26 and the connector compartment 30 carries a cable assembly 72 from the sensor delivery device 27 to the fiber optic connector member 32. A barrier 71 is provided in the channel 70 between the sensor delivery device 27 and the fiber optic connector member 32. The barrier is an aid to maintaining sterility during the calibration process and afterward until the package is fully open.

The gas-permeable, bacterial retentive Tyvek ™ cover 18 (FIG. 1), which overlies an upper face of the tray 12, is partially split, with a left-hand portion 18a covering the compartment 25 and the sensor delivery device compartment 26 to retain the device 27 therein. A right-hand portion 18b overlies the compartment 30 for the fiber optic connector member 32 and the compartment 34 for the filter 46. The cover 18 is adhered to the upper face of the tray 12 at its periphery to enclose and retain the sensor delivery device 27, the fiber optic connector member 32, and the filter 46 within the tray 12. The split between the cover portions 18a,18b is at the separation line 18c, to enable the user to selectively access the fiber optic connector member 32 and the filter 46 and its associated tubing during calibration of the sensor component 28.

Figure 4A:
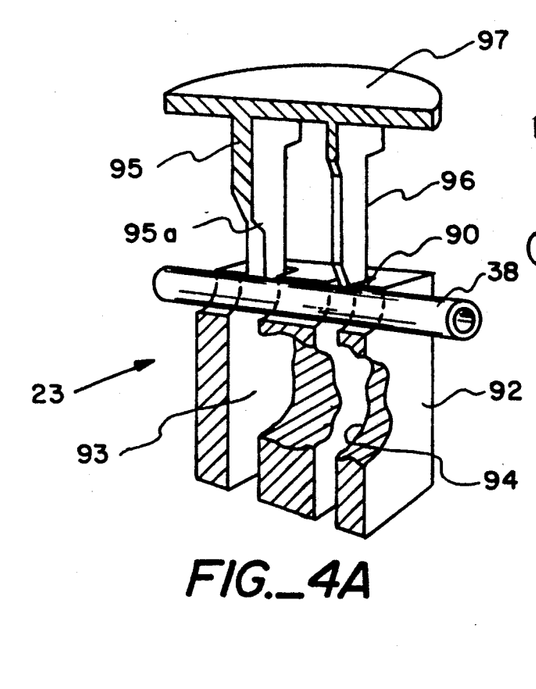
FIG. 4A is a perspective view, partially in section, of a guillotine valve used in the package and shown in an open position.
Figures 4B, 4C:
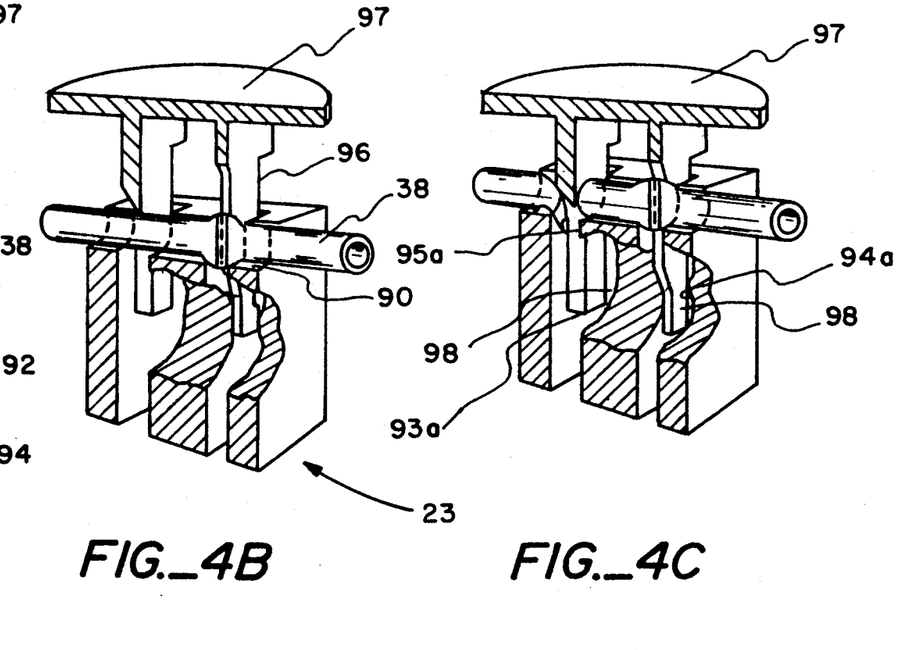
FIG. 4B is the partially closed position of the guillotine valve of FIG. 4A.
FIG. 4C is the fully closed position of the valve of FIG. 4A in which a section of the tubing trapped therein is severed.

Disposed between the hydration pouch 39 and the inlet 35 is a guillotine valve 23 better seen in FIGS. 4A-4C. Tubing 38 between the hydration pouch 39 and the liquid inlet fitting 35 extends through a channel 90 provided on valve body 92 shown partially in section in FIG. 4A. The valve body 92 is molded into the base plate 22a of the tonometry chamber 22. Slots 93, 94 provided in the valve body 92 receive respectively, a guillotine cutter 95 and a slide clamp 96 attached to an actuator 97 of the valve 23. As shown in FIG. 4B, as the actuator 97 descends, the slide clamp 96 in the slot 94 intrudes into the channel 90 to close off the tubing 38. As shown in FIG. 4C, further descent of the actuator 97 causes the guillotine blade 95a associated with the cutter 95 to slice through the tubing 38 aligned with the slot 93. In FIG. 4C, it can also be seen that escapement barbs 98 engage the respective rear walls 93a, 94a of the slots 93, 94 at the end of the downward stroke to hold the valve assembly 23 closed.

Figures 5A, 5C:
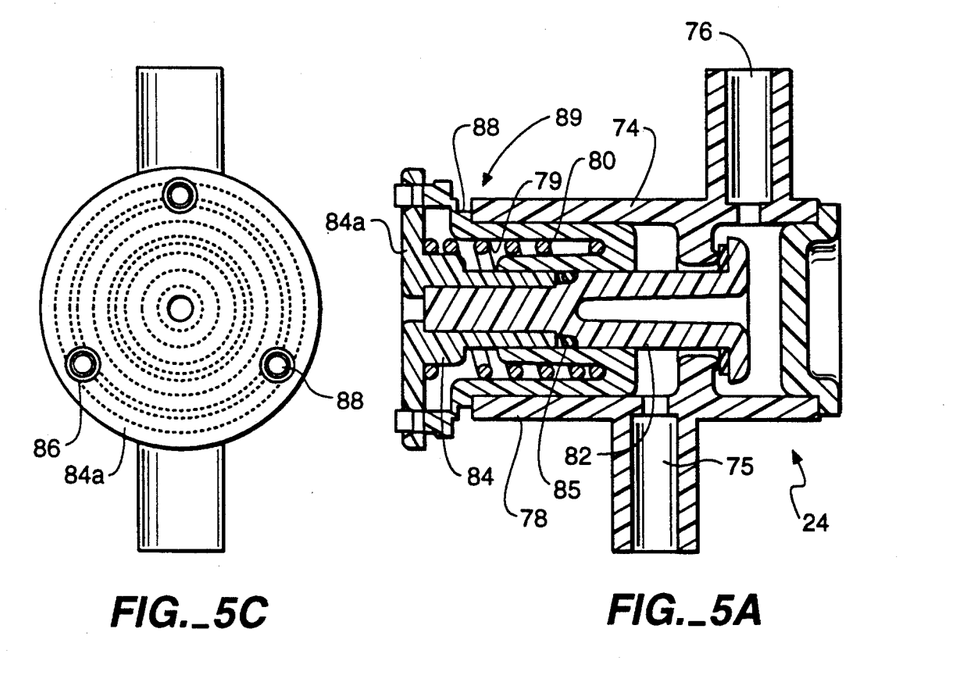
FIG. 5A is a sectional view of a frangible element valve incorporated in the package, the valve being built and assembled in a closed position.
FIG. 5C is an end view of the valve of FIGS. 5A and 5B.

The frangible valve assembly or valve 24 is better seen in FIGS. 5A-5E. The valve assembly 24 includes an outer sleeve 74 having an inlet passage 75 and an outlet passage 76 for conduction of either a fluid or a gas. Rigidly connected to the inner surface of the outer sleeve 74 is an inner sleeve 78 having an annular groove 79 therein. Disposed in the annular groove 79 is one end of a biasing spring 80. Coaxial with the inner sleeve 79 is a valve stem 82, an outer surface of which slidably extends through a passage 83 formed in the center of the inner sleeve 78 for the valve assembly 24. An upper portion of the valve stem 82 receives an actuator 84 rigidly mounted thereon to be coaxial with the valve stem 82. An O-ring seal 85 is placed in a space 85a provided between the valve stem 82 and the actuator 84 to assure proper seating of the O-ring seal 85. An outer end 84a of the actuator 84 includes three holes 86 disposed at spaced-apart intervals circumferentially around and just inside its perimeter (FIG. 5C). Three tabs 88 are connected to the inner sleeve 78 by a corresponding number of frangible elements 89. The tabs 88 align with the holes 86 in the outer end 84a of the actuator 84. As shown in FIG. 5A the valve assembly 24 is assembled with the spring 80 biasing the actuator 84 to the closed position with the actuator end 84a disposed outwardly from an inner end of each tab 88.

Figure 5B:
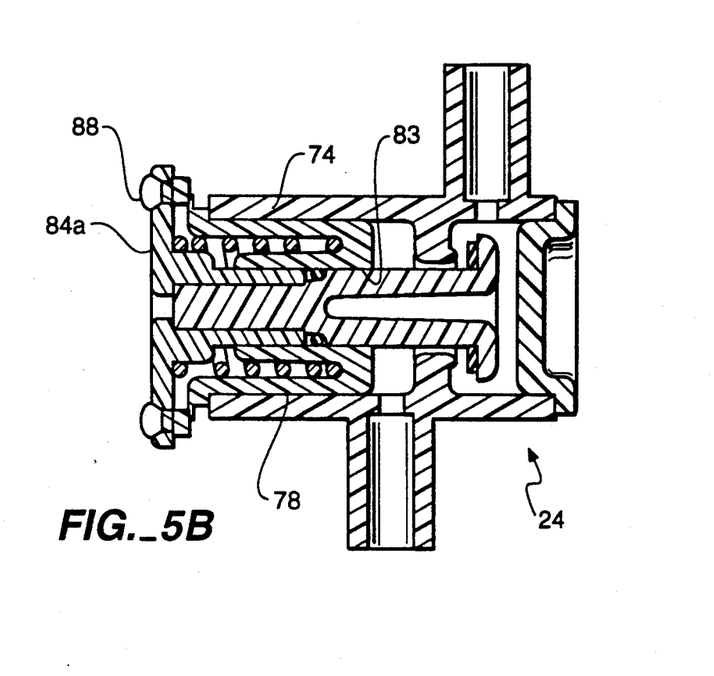
FIG. 5B is a view similar to the view of FIG. 5A, wherein the actuator of the valve is depressed to produce an open position of the valve.
Figure 5D:
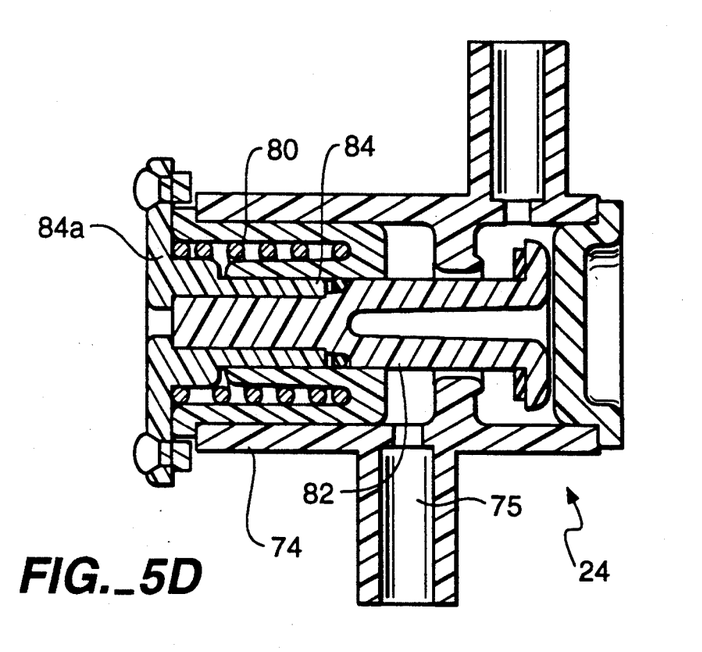
FIG. 5D is a section similar to FIG. 5A, wherein the valve is depressed to break the frangible elements.
Figure 5E:
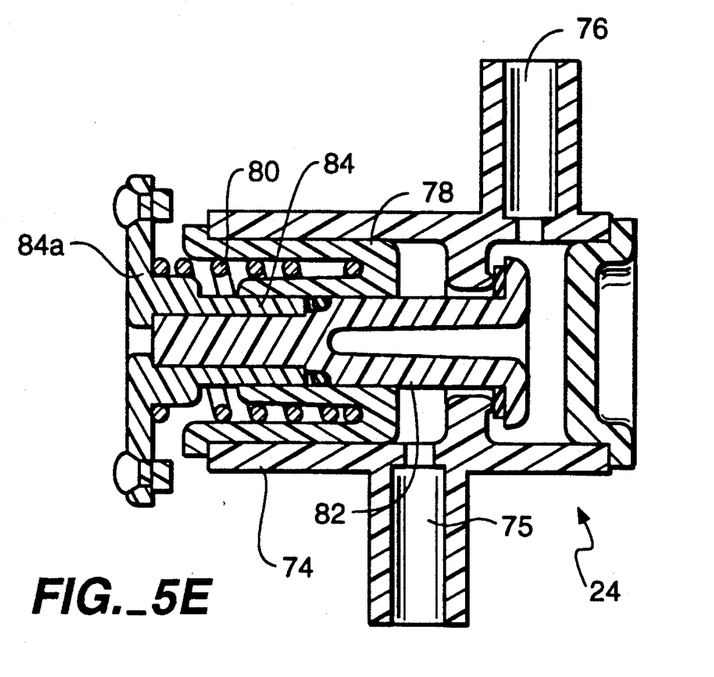
FIG. 5E is a view similar to the view of FIG. 5A wherein the valve is in the normally-closed position following breaking of the frangible elements.

As shown in FIG. 5B the actuator outer end 84a is moved downwardly on the tabs 88 to close the gap shown on the tabs in FIG. 5A and move the actuator 84 downwardly to place the valve assembly 24 in an open position. With the valve assembly 24 disposed in an open position, the ends of the tabs 88 are inserted through the holes 86 in the end 84a of the actuator 82. The tabs are then heated and deformed to flatten them and to hold the valve assembly 24 in a normally-open position. Alternative retaining means may also be used. To convert the normally open valve assembly 24 of FIG. 5B to a normally closed valve, the actuator 84 is further depressed as shown in FIG. 5D to break the frangible elements 89. As shown in FIG. 5E, this allows the spring 80 to move the outer end 84a and the associated actuator 84 outwardly to close the valve assembly 24 and cause the valve stem 82 to seal off a passage through the valve assembly 24. Once the frangible elements 89 have been broken, the valve assembly 24 remains closed until the actuator 84 is depressed by moving the outer end 84a against the biasing spring 80.

Figure 6A:
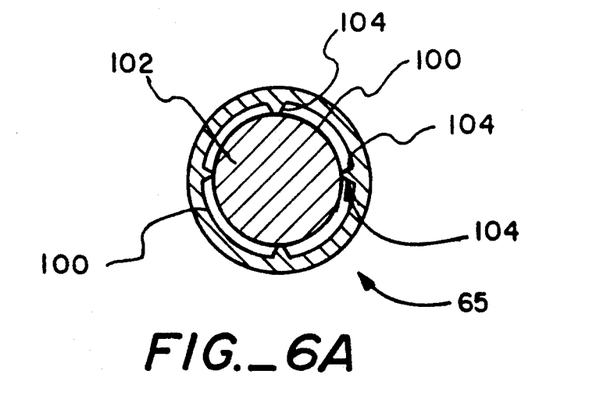
FIG. 6A is a sectional view of an in-line moisture filter taken along the lines 6A—6A of FIG. 2.
Figure 6B:
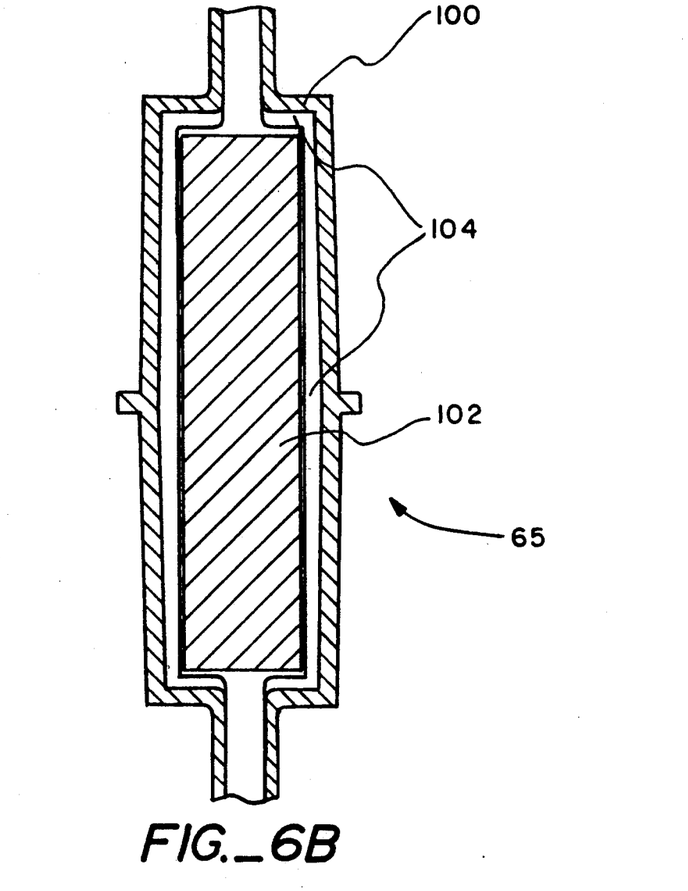
FIG. 6B is a sectional view taken along the lines 6B—6B of FIG. 2.

The in-line moisture filter 65 is shown in greater detail in FIGS. 6A, 6B. FIG. 6A is a cross sectional view taken along the lines 6A—6A in FIG. 2 and FIG. 6B is a longitudinal sectional view taken along the lines 6B—6B of FIG. 2. The in-line moisture filter 65 includes an outer housing 100 having disposed therein moisture absorbent material 102 that serves to remove water droplets from air or gas that is passing through the filter 65. The moisture absorbent material 102 is held centrally within the housing by a plurality of ribs 104, better seen in FIG. 6A, located within the inner diameter of the housing 100. The ribs 104 run longitudinally along the length of the absorbent material 102. In operation, the air or gas passing through the passages created between the ribs 104 and the absorbent material 102 is dried without experiencing a significant pressure drop from one end of the filter 65 to the other.

The filter 65 absorbs any overflow of hydration fluid from the tonometry chamber 22 and the plumbing associated therewith and yet is operable to pass gases therethrough during ETO sterilization, when the tonometry chamber 22 is vented, as well as when the calibration gases are pumped into the tonometry chamber 22. The principal advantage of the filter 65 is that the fluid cannot slosh out when the tray 12 is moved.. Next, gas vents through the Tyvek ™ cover 18, which also acts as a bacterial barrier to ingress of organisms back down the vent once calibration is over. The outer housing 100 is clear, to enable viewing of the absorbent material 102 therein. The absorbent material is colored, and changes colors when wet, to indicate the presence of moisture. Also, the presence of moisture in the filter 65 assists in maintaining the fluid level in the tonometry chamber 22 during storage.

Figure 7:
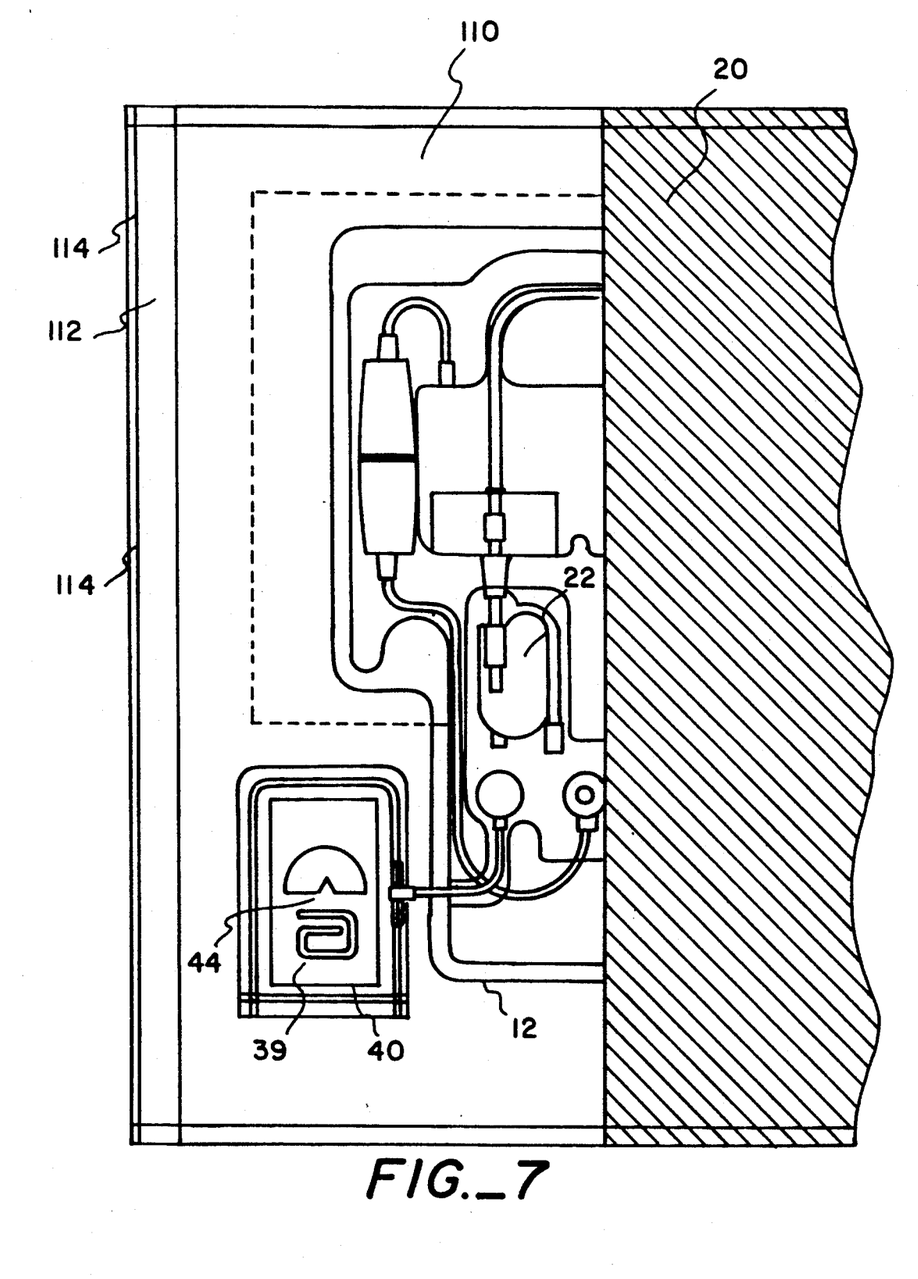
FIG. 7 is a top perspective view showing the packaging tray disposed in a sterilization pouch with a portion thereof visible through a window in the pouch and further showing a gas permeable Tyvek ™ membrane at the window area of the sterilization pouch.

The sterilization process is separate from the hydration process and is best understood by a consideration of FIG. 7. In FIG. 6, the tray 12 is inserted into a pouch or outer wrap 20 which is comprised mostly of foil but includes a clear window 110 and a gas-permeable, bacterial retentive strip 112. The pouch 20 is fully sealed on three sides and after the tray 12 is inserted therein, is sealed on the fourth side as shown at 114. With the tray 12 sealed in the pouch 20 as shown in FIG. 6, valves 23 and 24 are fully open. The hydration pouch 39 is gas-impermeable. With the pouch 20 sealed and the tray 12 in place, the tray 12 is then subjected to ETO sterilization, with the ETO gas flowing into the tray 12 through the gas-permeable, bacterial retentive strip 112. During ETO sterilization, in which the ETO gas is introduced through the gas permeable, bacterial retentive (Tyvek ™) strip 112 in the outer wrap 20 and through the Tyvek ™ cover 18 on the packaging tray 12, the tonometry chamber 22 and the plumbing associated therewith is open to the sterilization gases to sterilize the chamber 22, the tubing, the valves 23 and 24, the delivery device 27, the exterior of pouch 39, the reservoir 40, the pouch-popper 44 and the tubing sections 38 and 45 respectively associated with the delivery of hydration fluid and with the delivery of calibration gases into the tonometry chamber 22.

Figure 8:
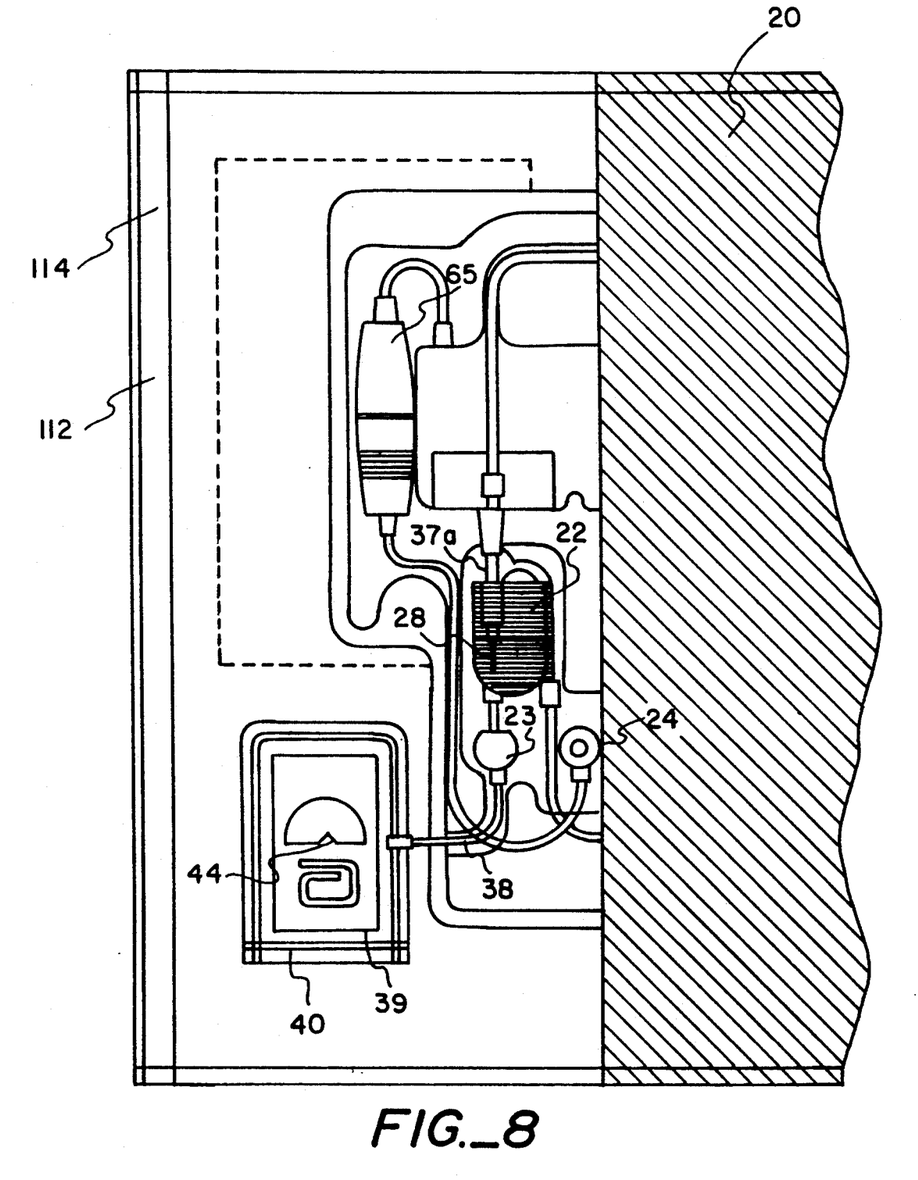
FIG. 8 is a top perspective view showing the hydration of the sensor component in the tonometry chamber through the rupturing of the hydration pouch following sterilization.

When the ETO sterilization procedure is complete and the gasses associated with ETO sterilization have dissipated or have been driven off from the tray 12 and the pouch 20, the hydration procedure is initiated as shown in FIG. 8. Valves 23 and 24 remain fully open and the hydration procedure is conducted within the sealed pouch 20 as shown in the visible portion thereof at the left side of FIG. 8. Pouch popper 44 is activated to rupture the hydration pouch 39 spilling the hydration fluid into the reservoir 40. The pouch is then squeezed until the hydration fluid is forced through the tubing 38, through the guillotine valve 23, and into the tonometry chamber 22.

The air in the tonometry chamber 22 is vented out through the upper fluid outlet fitting 37 and the tubing 52 through the compartment 26 associated with the sensor delivery device 27 as well as the side port 56. Excess fluid is conducted through the side port 56, through tubing 59, through the frangible valve 24 and into the in-line moisture filter 65. Excess fluid from the tonometry chamber 22 may also flow out through the gas inlet valve 36 through tubing 45 to the fitting 46. However, the hydrophobic filter 46 prevents fluid from flowing therethrough. Fluid is also present in the T-fitting 60 and is stopped by a hydroprobic filter 60a. The filter 65 also traps excess moisture in the absorbent material 102 provided therein.

Once the hydration of the sensor component 28 in the tonometry chamber 22 is complete, the guillotine valve 23 is actuated as shown in FIGS. 4A–4C to first close the tubing 38 and then to cut it to prevent further input of hydration fluid to the tonometry chamber 22. Then the frangible element valve 24 is first pushed to break the frangible elements 89, then released to close the valve 24 to prevent the loss of hydration fluid from the tonometry chamber 22. The guillotine valve 23 is operated through the pouch to maintain sterility of the tray 12 during hydration. The user is able to separate the hydration pouch 39 from the packaging tray 12 and simultaneously close the tonometry chamber 22 without damaging the integrity of the sterilization pouch 20 in which the packaging tray 12 is sealed.

Furthermore, the hydration pouch 39 and the gas permeable, bacterial retentive portion 112 of the sterilization pouch 20 can be separated from the packaging tray 12 to enable the fully hydrated sensor 28 to be sealed in a more compact, gas-impermeable sterilized pouch until it is ready for use. The "spent" hydration pouch 39 is unsightly and possibly confusing to the user.

The frangible element valve 24 enables the free flow of gas throughout the plumbing during the sterilization process, and the hydration process, and thereafter the frangible elements 89 are broken to produce a normally-closed, push-to-open valve 24 which seals the gas inlet 36 of the tonometry chamber 22. The valve 24 is also operated through the pouch 20. The valves 23 and 24 are also recessed within the tray 12 to prevent inadvertent operation.

Figure 9:
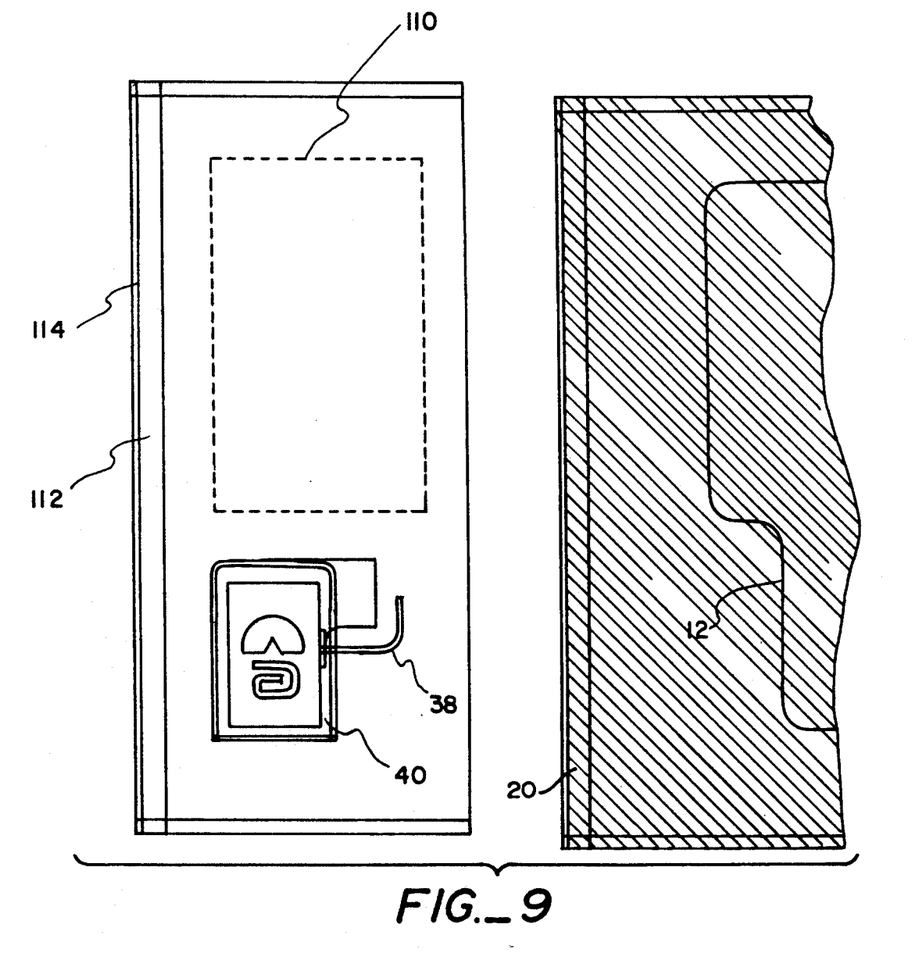
FIG. 9 is a top perspective view showing the overlapped window and the hydration pouch separated from the main body of the packaging tray, and the sterilization pouch resealed around the packaging tray.

With tubing 38 cut, and both valves 23 and 24 closed, the tray 12 holding a fully hydrated sensor component 28 can be resealed as shown in FIG. 9. The strap holding the reservoir 40 to the tray 12 is merely trapped between the tray 12 and the bottom plate 16. Therefore, with the tubing 38 cut, the reservoir 40 and the pouch 39 therein can be separated from the tray 12 to be disposed in the clear window 110 of the pouch 20 with the gas permeable, bacterial retentive Tyvek ™ strip 112. Thereafter, that portion of the pouch 20 can be cut away as shown in FIG. 8 and the pouch 20 resealed as at 116 to seal the tray 12 in a controlled sterile atmosphere impervious to gases and which also blocks out light. Although the clear window is useful during the in-pouch hydration step, the elimination of window 110 immediately thereafter, as shown herein, markedly increases storage times for the tray 12 and its associated sensor 28.

To calibrate the sensor component 28, the sterile tray 12 is removed from the sealed pouch of FIG. 9. The right-hand side 18b of the Tyvek ™ cover 18, partially split at 18c in FIG. 1, is removed to permit access to the fiber optic connector member 32 and the gas filter 46. The left-side 18a stays in place and, in cooperation with the sterile barrier 71, maintains the compartments 25 and 26, as well as the sensor delivery device 27 and the filter 65 in a sterile environment during calibration. The filter 46 is connected to a calibration device 120 (FIG. 10) to permit the infusion of gases containing the known analytes into the hydration fluid. Components of the calibration device 120 engage the tonometry chamber 22, first to open the valve 24 to permit the flow of calibration gases into the chamber 22, then to control the temperature of the hydration fluid in the tonometry chamber 22 during the calibration process.

The tonometry chamber 22 is designed as a gas-driven, circulating loop. The needle orifice 36a bubbles the calibration gases into the chamber 22, with the baffle 19 provided in the middle of the chamber 22 enhancing circulatory motion of the hydration fluid around the baffle 19, and also preventing the bubbles generated in the hydration fluid through the needle orifice 36a from impinging on the sensor component 28, thus to minimize the erratic response thereof during calibration. The baffle 19 also permits a reduction in chamber volume by taking up buffer volume. The turbulence generated by the circulating loop also promotes better mixing of the liquid with the gas, thus to decrease the time needed for gas equilibration. Mixing is also necessary for uniform heating, i.e., temperature control.

The gas pressure in the chamber 22 creates a movement of fluid out of the filled calibration chamber 22 at first, leaving behind an optimum amount of fluid for fast mixing. Fluid and gas does not mix well in a filled chamber. Also, the level of the fluid must remain above the level of the internal baffle 19 to maximize the mixing action. As fluid moves out of the chamber 22, the fluid level drops from 50mm (filled) to 30mm in less than ten seconds, and stays at the lower level for the remainder of the calibration. The excess fluid is absorbed by the filter 65. The amount of fluid remaining in the chamber is controlled by the height and geometry of the gas outlet port 37.

Figure 10:
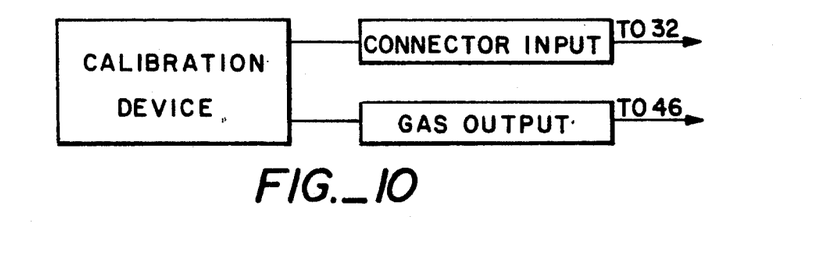
FIG. 10 is a representation of the calibration device in block-diagram form.

The connector member 32 is also connected to the calibration device 120 to compare the readouts during equilibration of the hydration fluid to the known valves of the analytes used for calibration. For convenience, the compartment 30 holding the member 32 during storage is also sized to hold an optical receptacle (not shown) of the calibration device 120 during calibration.

The packaging technique of the present invention allows a blood gas catheter to be calibrated immediately prior to use without the need of a blood gas analyzer to obtain reference calibrant values. The calibration technique is practical and allows calibration using aseptic handling that protects the cleanliness of the medical device and minimizes the possibility of contamination of the sensor component.

Having defined a preferred embodiment of the invention it should be understood that other embodiments are possible. The configuration of the sensor component of a specific device may dictate alternative configurations for the packaging.

We claim:

1. An improved package for a medical device that includes a hydratable sensor, said package comprising:
    a tray for receiving the medical device;
    a chamber provided within the tray for receiving a hydratable sensor of the medical device;
    a hydratable sensor of the medical device, said sensor disposed in the chamber;
    a gas permeable cover overlying the tray;
    a source of hydration fluid external to the tray;
    an outer wrap including a gas-impermeable portion and a gasimpermeable portion enclosing the tray; and
    plumbing means for controlling fluid flow into and within the outer wrap, said plumbing means being operable to selectively establish, without breaching a portion of the outer wrap surrounding the sensor, fluid communication between:
    a. said gas permeable portion of the outer wrap and said sensor of effect sterilization of said sensor with a gaseous sterilant;
    b. said chamber and the source of hydration fluid external to the tray to effect hydration of said sensor with the hydration fluid; and
    c. said chamber and a source of gas external to the chamber and the hydration fluid therein to effect equilibration of the hydration fluid in order to calibrate the sensor within the chamber.

2. The improved package according to claim 1, wherein the source of hydration fluid comprises a rupturable pouch that includes a port connected in fluid communication with the chamber so that the hydration fluid is delivered to the chamber when the pouch is ruptured.

3. The improved package according to claim 1, wherein the source of hydration fluid is, at least initially, enclosed within the outer wrap.

4. The improved package according to claim 3, wherein the external source of hydration fluid is received in the gas-permeable portion of the outer wrap, and, after the hydration fluid flows into the chamber, said gas-permeable portion of the outer wrap is severed from the gas-impermeable portion of the outer wrap, and the tray is sealed in said gas-impermeable portion, thereby maintaining the sensor in a sterile condition while the medical device is stored, prior to use of the sensor.

5. The improved package according to claim 4, wherein the portion of the outer wrap in which the source of hydration fluid is disposed includes a window portion which is useful to effect hydration of the sensor, and the gas-impermeable portion of the outer wrap being impervious to light after the window is removed, thus to substantially increase storage times for the tray and the sensor within the gas-impermeable outer wrap.

6. The improved package according to claim 1, wherein the plumbing means include a calibration fluid line connected in fluid communication with the chamber, and wherein the tray includes means for providing access to the calibration fluid line so that the source of the gas used for equilibration of the hydration fluid can be connected to supply the gas to the chamber for calibration of the sensor, while continuing to maintain the sensor in the sterile condition.

7. The improved package according to claim 1, wherein the plumbing means include a first valve disposed between the source of hydration fluid and the chamber, and wherein the first valve is open while the hydration fluid is supplied to the chamber, and thereafter, is closed, severing the source of the hydration fluid from the tray.

8. The improved package according to claim 1, wherein the plumbing means include a second valve that is initially held open and is disposed in a line provided to connect to the source of the gas used to effect equilibration of the hydration fluid, a first closure of the second valve converting it to a normally-closed valve.

9. The improved package according to claim 8, wherein the plumbing means include a moisture filter disposed in a fluid path, between the second valve and a portion of the tray proximate its gas-permeable cover, so that moisture is removed from a gas passing through the second valve before the gas passes to the tray and through the gas-permeable membrane.

10. The improved package according to claim 1, wherein the chamber comprises a tonometry chamber having a smoothly curved wall disposed adjacent to a port through which the gas used toe effect equilibration of the hydration fluid enters, the curved wall promoting turbulence in the hydration fluid as the gas flows through the chamber, but generally assisting in preventing gas bubbles from impinging upon the sensor.

11. In a package for a sterilizable calibratable medical device, a tonometry chamber receiving a sensor component of the medical device, the tonometry chamber comprising:
    a small compartment having a curved wall, a fluid inlet port, a gas inlet port and a gas vent; a baffle disposed between the fluid inlet port and the gas inlet port, the curved wall of the chamber and the baffle combining to promote circulatory flow of the fluid disposed therein.

12. A tonometry chamber as claimed in claim 11, which includes an oversized base supporting an upper fluid holding portion of the chamber, the base including a step-in portion at a lower end of the chamber, the step-in portion supporting a first valve associated with the liquid inlet port and a second valve associated with the gas inlet port, the base and its step-in portion providing a fixed relation between the tonometry chamber and the first and second valves.

13. A tonometry chamber as claimed in claim 12, wherein the sensor component intrudes into the tonometry chamber through the gas vent, the baffle is disposed between the sensor component and the gas inlet port, and the gas inlet port includes a needle-point orifice promoting turbulent flow of the fluid in the tonometry chamber through the inlet of gas therein, such turbulent flow accelerating the equilibration of the fluid in the tonometry chamber, with the baffle between the sensor component and the needle-point orifice minimizing the impingement of gas bubbles on the sensor component.

14. A tonometry chamber as claimed in claim 13, wherein the gas outlet port includes a sensor guide tube, for supporting an outer end of the sensor within the tonometry chamber.

15. A tonometry chamber as claimed in claim 14, wherein the gases input to the chamber vent off a portion of the hydration fluid in the chamber during calibration, with the fluid level in the chamber to be maintained above the upper level of the baffle therein to maximize mixing efficiency.

16. A method of packaging a medical device that includes a hydratable sensor, the method comprising the steps of:
   providing a tray for receiving the medical device;
   defining a chamber within the tray for receiving a hydratable sensor of the medical device;
   providing a hydratable sensor on the medical device, said sensor disposed in the chamber;
   providing a gas-permeable cover overlying the tray;
   providing a source of hydration fluid external to the tray;
   providing an outer wrap including a gas-permeable portion and a gas-impermeable portion enclosing the tray; and
   providing plumbing means for controlling fluid flow into and within the outer wrap, said plumbing means being operable to selectively establish, without breaching a portion of the outer wrap surrounding the sensor, fluid communication between:
   a. said gas-permeable portion of the outer wrap and said sensor to effect sterilization of said sensor with a gaseous sterilant;
   b. said chamber and the source of hydration fluid external to the tray to effect hydration of said sensor with the hydration fluid; and
   c. said chamber and a source of gas external to the chamber and the hydration fluid therein to effect equilibration of the hydration fluid in order to calibrate the sensor within the chamber.

17. The method according to claim 16, including the steps of storing the hydration fluid in a rupturable pouch, and connecting a portion in the pouch with the chamber, so that the hydration fluid is delivered to the chamber when the pouch is ruptured.

18. The method according to claim 17, including the step of disposing a window portion in a gas-permeable portion of the outer wrap in which the source of hydration fluid is disposed, the window portion useful to effect hydration of the sensor, and the sealed portion of the pouch being impervious to light after the window is removed, thus to substantially increase storage times for the tray and the sensor within the sealed pouch.

19. The method according to claim 18, including the step of severing a gas-permeable portion of the outer wrap in which the pouch containing hydration fluid is disposed from a gas-impermeable portion of the outer wrap in which the tray is sealed, after the hydration fluid flows into the chamber from the rupturable pouch containing the hydration fluid.

20. The method according to claim 16, including the step of disposing the pouch containing hydration fluid external to the tray, but at least initially, enclosing said pouch within the outer wrap.

21. The method according to claim 16, including the steps of providing access to a calibration f line in fluid communication with the chamber, and connecting the calibration fluid line to the source of the gas used for equilibration of the hydration fluid to supply the gas to the chamber for calibration of the sensor, while continuing to maintain the sensor in the sterile condition.

22. The method according to claim 16, including the step of disposing a first valve between the source of hydration fluid and the chamber, wherein the first valve is open while the hydration fluid is supplied to the chamber, and thereafter is closed, severing the source of hydration fluid from the tray.

23. The method according to claim 22, including the step of disposing a second valve that is initially held open in a line provided to connect the source of the gas used to effect equilibration of the hydration fluid, a first closure of the second valve converting it to a normally-closed valve.

24. The method according to claim 22, including the step of disposing a moisture filter disposed in a fluid path, between the second valve and a portion of the tray proximate gas-permeable cover, so that moisture is removed from a gas passing through the second valve before the gas passes to the tray and through the gas-permeable membrane.

25. The method according to claim 16, including the step of disposing a smoothly curved wall in the chamber, adjacent to a port through which the gas used to effect equilibration of the hydration fluid enters, the curved wall to promote turbulence in the hydration fluid as the gas flows through the chamber, but generally to assist in preventing gas bubbles from impinging upon the sensor.

* * * * *